(12) United States Patent
Lipson et al.

(10) Patent No.: US 11,859,972 B2
(45) Date of Patent: ***Jan. 2, 2024

(54) MICRORESONATOR-FREQUENCY-COMB-BASED PLATFORM FOR CLINICAL HIGH-RESOLUTION OPTICAL COHERENCE TOMOGRAPHY

(71) Applicant: The Trustees of Columbia University in the City of New York, New York, NY (US)

(72) Inventors: Michal Lipson, New York, NY (US); Xingchen Ji, New York, NY (US); Alexander Klenner, New York, NY (US); Xinwen Yao, Baltimore, MD (US); Yu Gan, Harriston, NJ (US); Alexander L. Gaeta, New York, NY (US); Christine P Hendon, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/367,884

(22) Filed: Jul. 6, 2021

(65) Prior Publication Data

US 2022/0128346 A1 Apr. 28, 2022

Related U.S. Application Data

(63) Continuation of application No. 16/100,401, filed on Aug. 10, 2018, now Pat. No. 11,092,424.

(60) Provisional application No. 62/607,825, filed on Dec. 19, 2017, provisional application No. 62/540,412, filed on Aug. 2, 2017.

(51) Int. Cl.
*G01B 9/02001* (2022.01)
*G01B 9/02091* (2022.01)

(52) U.S. Cl.
CPC ..... *G01B 9/02008* (2013.01); *G01B 9/02091* (2013.01)

(58) Field of Classification Search
CPC .................. G01B 9/02008; G01B 9/02091
See application file for complete search history.

(56) References Cited

U.S. PATENT DOCUMENTS

| 7,519,253 | B2 | 4/2009 | Islam |
| 7,695,140 | B2 | 4/2010 | Fercher |
| 2008/0018906 | A1 | 1/2008 | Kurokawa et al. |
| 2010/0220334 | A1 | 9/2010 | Condit et al. |

(Continued)

OTHER PUBLICATIONS

Savchenkov et al., "Kerr combs with selectable central frequency," Nat. Photonics., vol. 5 2011, pp. 293-296.

(Continued)

*Primary Examiner* — Michael A Lyons
(74) *Attorney, Agent, or Firm* — BakerHostetler

(57) ABSTRACT

A method of providing optical coherence tomography (OCT) imaging may comprise using an on-chip frequency comb source interfaced with an OCT system by a circulator as an imaging source and reconstructing OCT images from resulting spectral data from target tissue illuminated by the imaging source.

20 Claims, 9 Drawing Sheets

(56) References Cited

U.S. PATENT DOCUMENTS

| | | | |
|---|---|---|---|
| 2011/0235045 A1* | 9/2011 | Koerner | G02B 21/0056 356/451 |
| 2011/0292399 A1 | 12/2011 | Alphonse | |
| 2012/0177060 A1 | 7/2012 | Lipson et al. | |
| 2015/0323450 A1* | 11/2015 | Lipson | H01L 31/02327 438/69 |
| 2016/0134078 A1* | 5/2016 | Gaeta | H01S 5/5063 372/20 |
| 2018/0011249 A1 | 1/2018 | Zhu et al. | |
| 2018/0083414 A1 | 3/2018 | Weiner et al. | |
| 2018/0205463 A1* | 7/2018 | Karpov | G02F 1/073 |
| 2019/0391415 A1 | 12/2019 | Lipson et al. | |

OTHER PUBLICATIONS

Smirnov et al., "Optical spectral broadening and supercontinuum generation in telecom applications," Optical Fiber Technology, vol. 12, Issue 2, Apr. 2006, pp. 122-147.

Suh et al., "Microresonator soliton dual-comb spectroscopy," Science, vol. 354, 2016, pp. 600-603.

Tearney et al., "Consensus Standards for Acquisition, Measurement, and Reporting of Intravascular Optical Coherence Tomography Studies," J. Am. Coll. Cardiol., vol. 59, 2012, pp. 1058-1072.

Wang et al., "Mid-infrared optical frequency combs at 2.5 µm based on crystalline microresonators," Nat. Commun., vol. 4, 1345, 2013.

Wang, Ling et al. "Graphics processing unit-based dispersion encoded full-range frequency-domain optical coherence tomography". Journal of Biomedical Optics, vol. 17(7), 077007, Jul. 2012, pp. 077007-1-077007-7. (Year: 2012).

Xue et al., "Microresonator Kerr frequency combs with high conversion efficiency," Laser Photonics Rev., 11, n/a-n/a, 2017.

Xue et al., "Mode-locked dark pulse Kerr combs in normal-dispersion microresonators," Nat. Photonics, vol. 9, 2015, pp. 594-600.

Yao et al., "Visualization and tissue classification of human breast cancer images using ultrahigh-resolution OCT," Lasers Surg. Med., vol. 49, 2017, pp. 258-269.

Adler et al., "Ultrahigh resolution optical coherence tomography imaging with a broadband superluminescent diode light source," Optics Express, vol. 12, Issue 10, May 2004, pp. 2112-2119.

Assayag et al., "Large Field, High Resolution Full-Field Optical Coherence Tomography," Technol. Cancer Res. Treat., vol. 13, 2014, pp. 455-468.

Coen et al., "Modeling of octave-spanning Kerr frequency combs using a generalized mean-field Lugiato-Lefever model," Opt. Lett., vol. 38, 2013, pp. 37-39.

Corwin et al., "Fundamental amplitude noise limitations to supercontinuum spectra generated in a microstructured fiber," Appl. Phys. B., vol. 77, 2003, pp. 269-277.

Cundiff et al., "Colloquium: Femtosecond optical frequency combs," Rev. Mod. Phys., vol. 75, 325, 2003.

Del'Haye et al., "Octave Spanning Tunable Frequency Comb from a Microresonator," Phys. Rev. Lett., vol. 107, 2011.

Del'Haye et al., "Optical frequency comb generation from a monolithic microresonator," Nature 450, 2007, pp. 1214-1217.

Diddams et al., "Direct link between microwave and optical frequencies with a 300 THz femtosecond laser comb," Phys. Rev. Lett., vol. 84, 5102, 2000.

Drexler et al., "In vivo ultrahigh-resolution optical coherence tomography," Opt. Lett., vol. 24, 1999, pp. 1221-1223.

Dutt et al., "Dual-comb spectroscopy using on-chip mode-locked frequency combs," Photonics.com, Mar. 26, 2013.

Dutt et al., "On-chip dual comb source for spectroscopy," Optics, Nov. 2016.

Ferdous et al., "Spectral line-by-line pulse shaping of on-chip microresonator frequency combs," Nat. Photonics, vol. 5, 2011, pp. 770-776.

Froehly et al., "Supercontinuum sources in optical coherence tomography: A state of the art and the application to scan-free time domain correlation techniques and depth dependant dispersion compensation," Opt. Fiber Technol., vol. 18, 2012, pp. 411-419.

Gan et al., "Analyzing three-dimensional ultrastructure of human cervical tissue using optical coherence tomography," Biomed. Opt. Express, vol. 6, 2015, pp. 1090-1108.

Gan et al., "Automated classification of optical coherence tomography images of human atrial tissue," J. Biomed. Opt., vol. 21, 2016, pp. 101407-101407.

Garcia-Garcia et al., "Virtual histology and optical coherence tomography: from research to a broad clinical application," Heart, vol. 95, 2009, pp. 1362-1374.

Genty et al., "Fiber supercontinuum sources (Invited)," Josa B., vol. 24, 2007, pp. 1771-1785.

Griffith et al., "Coherent mid-infrared frequency combs in silicon-microresonators in the presence of Raman effects," Optics Express, vol. 24, Issue 12, 2016, pp. 13044-13050.

Griffith et al., "Silicon-chip mid-infrared frequency comb generation," Nat. Commun., 2015, 6: 6299.

Grudinin et al., "Generation of optical frequency combs with a CaF 2 resonator," Opt. Lett., vol. 34, 2009, pp. 878-880.

Hausmann et al., "Diamond nonlinear photonics," Nat. Photonics, vol. 8, 2014, pp. 369-374.

Hee et al., "Optical coherence tomography of the human retina," Arch. Ophthalmol., vol. 113, 1995, pp. 325-332.

Herr et al., "Mode Spectrum and Temporal Soliton Formation in Optical Microresonators," Phys. Rev. Lett., vol. 113, 2014.

Herr et al., "Universal formation dynamics and noise of Kerr-frequency combs in microresonators," Nat. Photonics, vol. 6, 2012, pp. 480-487.

Hsiung et al., "Benign and malignant lesions in the human breast depicted with ultrahigh resolution and three-dimensional optical coherence tomography," Radiology, vol. 244, 2007, pp. 865-874.

Huang et al., "Optical coherence tomography," Sci. N. Y. NY 254, 1178 (1991).

Huang et al., "Smooth and flat phase-locked Kerr frequency comb generation by higher order mode suppression," Sci. Rep., vol. 6, 2016.

Ikeda et al., "Thermal and Kerr nonlinear properties of plasma-deposited silicon nitride/silicon dioxide waveguides," Opt. Express, vol. 16, 2008, pp. 12987-12994.

Ji et al., "Chip-Based Frequency Combs for High-Resolution Optical Coherence Tomography," in Conference on Lasers and Electro-Optics, OSA Technical Digest (online) (Optical Society of America, 2018), paper STh1J.4.

Ji et al., "Ultra-low-loss on-chip resonators with sub-milliwatt parametric oscillation threshold," Optics, vol. 4, Issue 6, Jun. 2017, pp. 619-624.

Joshi et al., "Thermally controlled comb generation and soliton modelocking in microresonators," Opt. Lett., vol. 41, 2016, pp. 2565-2568.

Jung et al., "Optical frequency comb generation from aluminum nitride microring resonator," Opt. Lett., vol. 38, 2810, 2013.

Kippenberg et al., "Kerr-Nonlinearity Optical Parametric Oscillation in an Ultrahigh-Q Toroid Microcavity," Phys. Rev. Lett., vol. 93, 2004.

Kippenberg et al., "Microresonator-based optical frequency combs," Science, vol. 332, 2011, pp. 555-559.

Klenner et al., "Gigahertz frequency comb offset stabilization based on supercontinuum generation in silicon nitride waveguides," Optics Express, vol. 24, Issue 10, 2016, pp. 11043-11053.

Kuyken et al., "An octave-spanning mid-infrared frequency comb generated in a silicon nanophotonic wire waveguide," Nat. Commun., vol. 6, 6310, 2015.

Lamont et al., "Route to stabilized ultrabroadband microresonator-based frequency combs," Opt. Lett., vol. 38, 2013, pp. 3478-3481.

Lamouche et al., "Intravascular optical coherence tomography on a beating heart model," J. Biomed. Opt., vol. 15, 046023, 2010.

Lee et al., "Optimization for axial resolution, depth range, and sensitivity of spectral domain optical coherence tomography at 1.3 µm," Journal of the Korean Physical Society, vol. 55, Issue 6, Dec. 2009, pp. 2354-2360.

(56) References Cited

OTHER PUBLICATIONS

Leitgeb et al., "Performance of fourier domain vs. time domain optical coherence tomography," Opt. Express, vol. 11, 2003, pp. 889-894.

Marin-Palomo et al., "Microresonator-based solitons for massively parallel coherent optical communications," Nature, vol. 546, 2017, pp. 274-279.

Matsko et al., "Optical hyperparametric oscillations in a whispering-gallery-mode resonator: Threshold and phase diffusion," Phys. Rev., A 71, 2005.

Miller et al., "Low-loss silicon platform for broadband mid-infrared photonics," Optica, vol. 4, Issue 7, 2017, pp. 702-712.

Miller et al., "On-chip frequency comb generation at visible wavelengths via simultaneous second- and third-order optical nonlinearities," Opt. Express, vol. 22, 26517, 2014).

Nguyen et al., "Intraoperative evaluation of breast tumor margins with optical coherence tomography," Cancer Research, vol. 69, Issue 22, Nov. 2009, pp. 8790-8796.

Okawachi et al., "Octave-spanning frequency comb generation in a silicon nitride chip," Opt. Lett., vol. 36, 2011, pp. 3398-3400.

Pfeiffer et al., "Octave-spanning dissipative Kerr soliton frequency combs in $Si_3N_4$ microresonators," Optica., vol. 4, 684, 2017.

Pu et al., "Efficient frequency comb generation in AlGaAs-on-insulator," Optica., vol. 3, 823, 2016.

Savastru et al., "Detection of breast surgical margins with optical coherence tomography imaging: a concept evaluation study," J. Biomed. Opt., vol. 19, 2014, pp. 056001-056001.

Gaeta et al., "E2CDA: Type I: Collaborative Research: Energy efficient computing with chip-based photonics", NSF Award #: 16401088, Last Modified Date: May 2021.

* cited by examiner

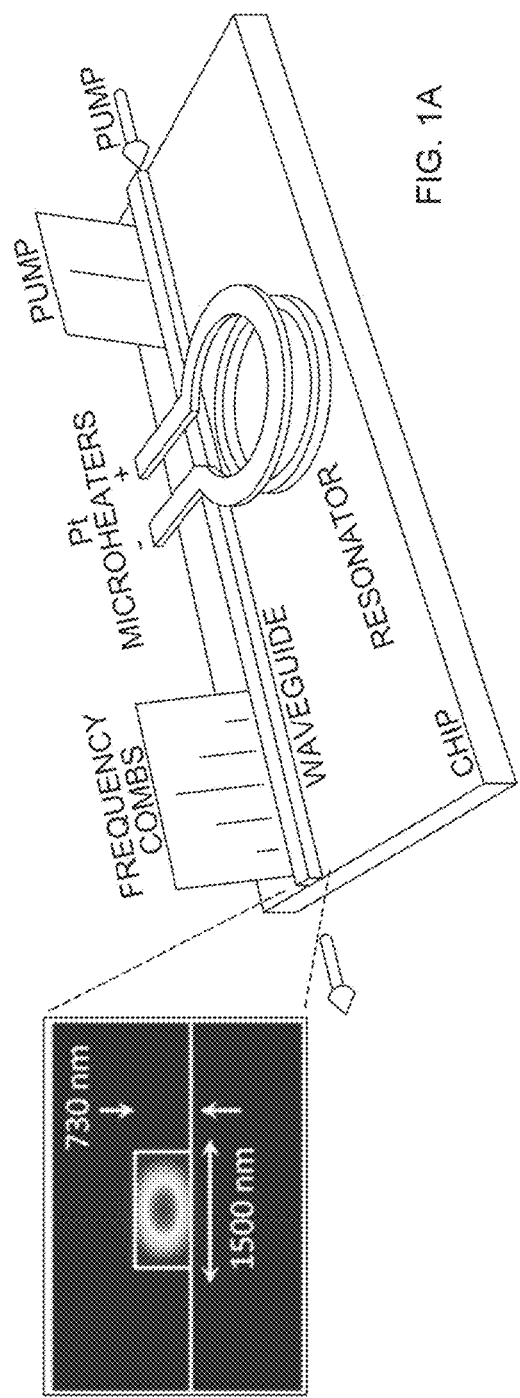
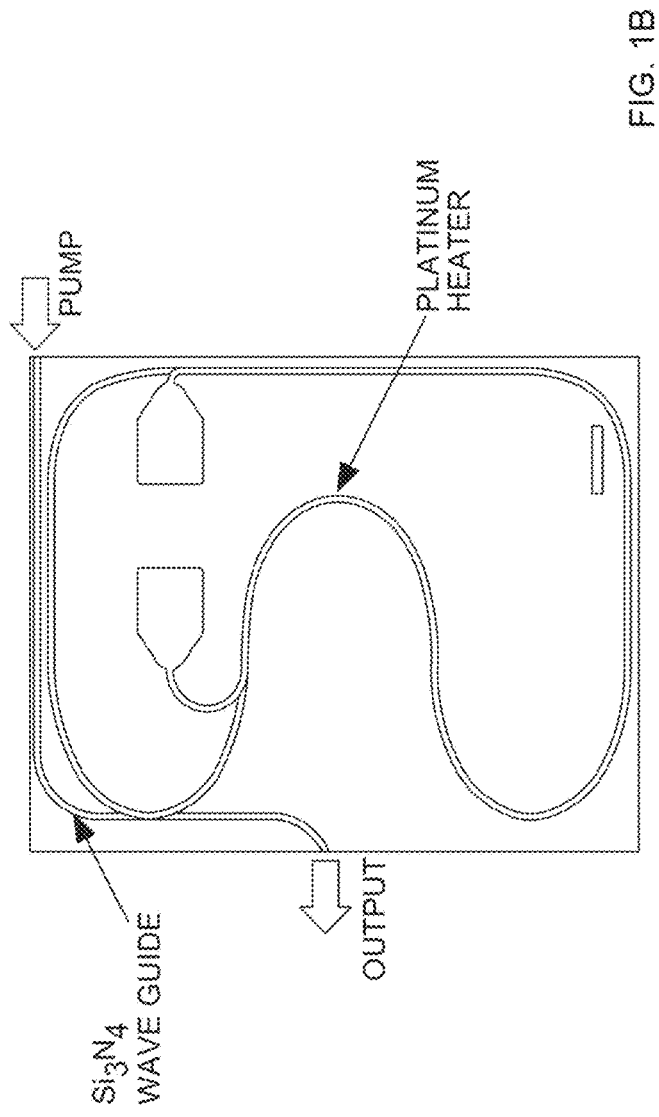
FIG. 1A
FIG. 1B

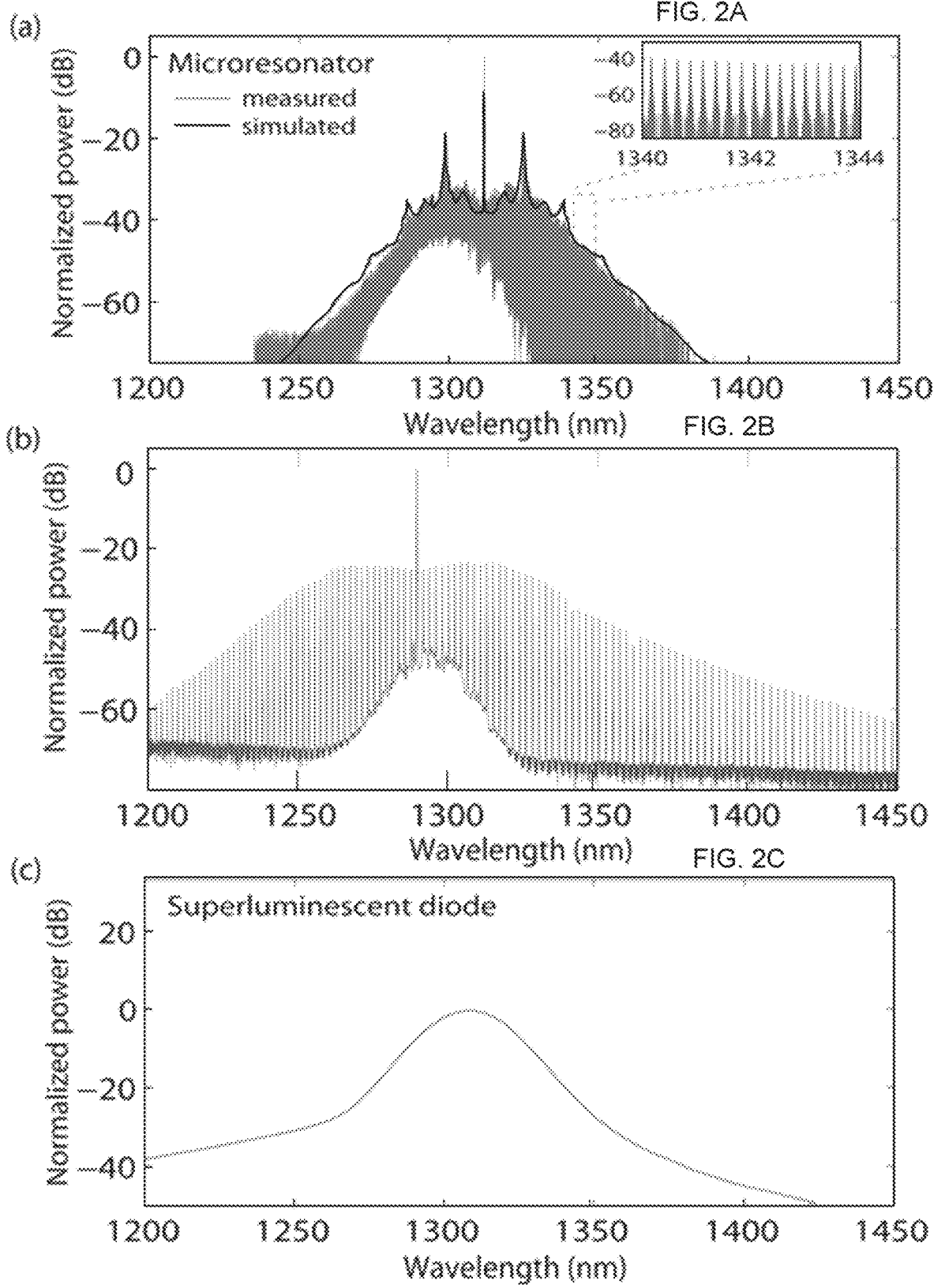

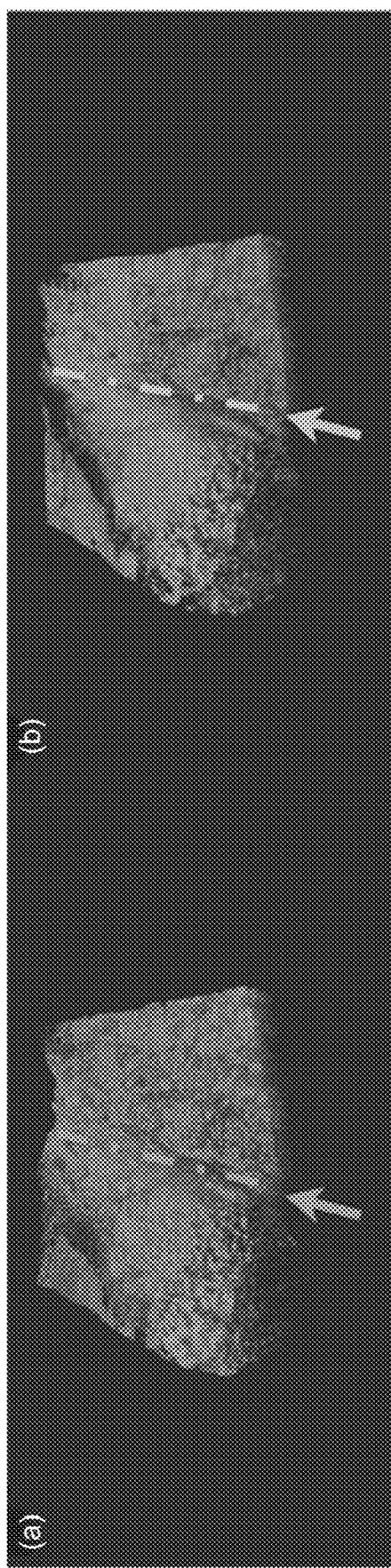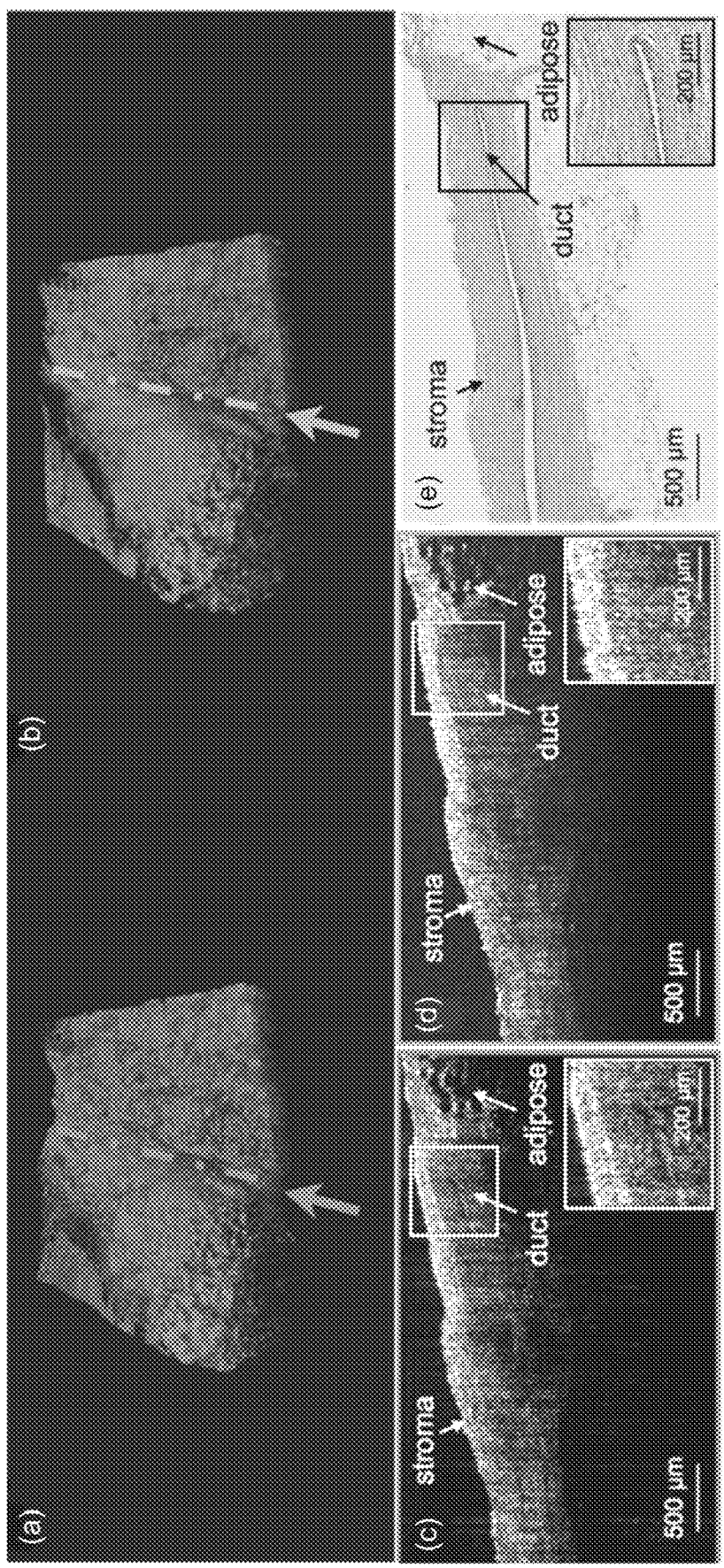

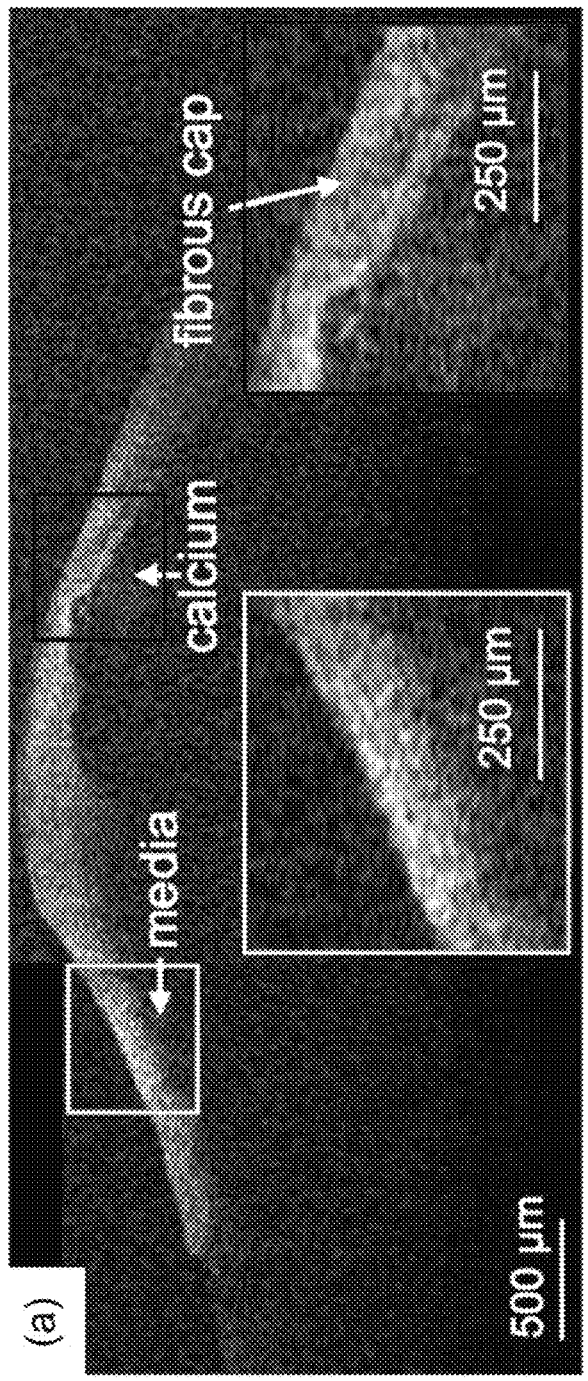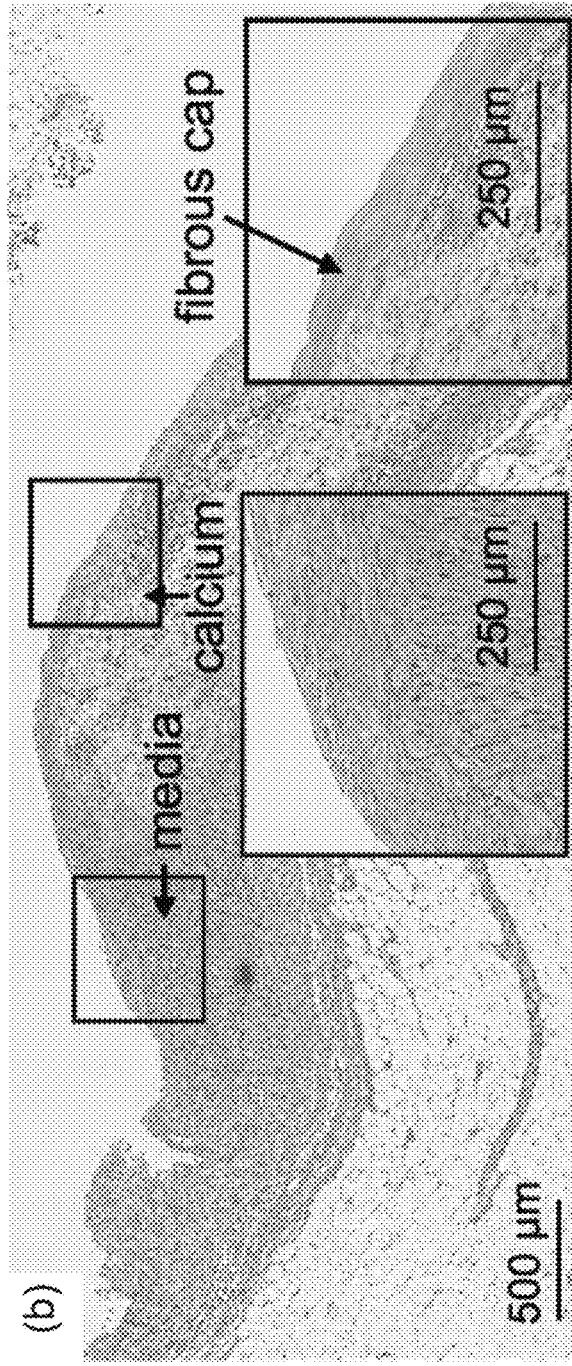
FIG. 4A
FIG. 4B

MICRORESONATOR-FREQUENCY-COMB-BASED PLATFORM FOR CLINICAL HIGH-RESOLUTION OPTICAL COHERENCE TOMOGRAPHY

CROSS-REFERENCE TO RELATED APPLICATIONS

The present application is a Continuation Application which claims priority to application Ser. No. 16/100,401 (filed Aug. 10, 2018) which claims the benefit of U.S. Provisional Application No. 62/540,412 (filed Aug. 2, 2017) and U.S. Provisional Application No. 62/607,825 (filed Dec. 19, 2017), each of which are incorporated herein by reference in their entireties for any and all purposes.

GOVERNMENT RIGHTS

This invention was made with government support under contract $N_{66001}$-16-1-4052 awarded by the Defense Advanced Research Projects Agency; contract FA9550-15-1-0303 awarded by the Air Force Office of Scientific Research; contract 2016-EP-2693-A, CCF-1640108 awarded by the National Science Foundation; and contract 1DP2HL127776-01 awarded by the National Institutes of Health. The government has certain rights in the invention.

TECHNICAL FIELD

A microresonator-frequency-comb-based platform for optical coherence tomography provides both deep signal penetration and ultra-high resolution (UHR) with clinically safe powers. Real-time spectral domain optical coherence tomography (SD-OCT) imaging of human tissue is provided using on-chip frequency combs.

BACKGROUND

Optical coherence tomography (OCT) is a non-invasive interferometric imaging modality that provides depth-resolved, high-resolution cross-sectional and three-dimensional images of tissue microstructure with micrometer-scale axial resolution in real-time. OCT enables subsurface imaging of depths 1-2 mm in tissue with high spatial resolution in three dimensions and high sensitivity in vivo. Fiber-based OCT systems can be incorporated into catheters to image internal organs. These features have made OCT a powerful tool for medical imaging. OCT has revolutionized fields such as ophthalmology and cardiology with noninvasive real-time micron scale resolution imaging.

Despite their continuous advancements, current OCT systems cannot simultaneously achieve both deep signal penetration and ultra-high resolution (UHR) because of the limitations constituted by the available light sources for clinical settings. Many medical imaging applications such as tumor margin detection for breast cancer diagnosis and treatment would benefit from a safe light source with the two key performance factors: broad optical bandwidth and long central wavelength. While conventional UHR-OCT systems rely on sources around 800 nm wavelength, working at longer wavelengths (above 1 µm) provide deeper signal penetration due to reduced Rayleigh scattering inside the biological tissue. Axial resolutions below 5 µm require sources with a full-width half-maximum (FWHM) bandwidths of more than 100 nm. This requirement of broadband source becomes more stringent for longer wavelength regime, which yet favors deeper signal penetration due to reduced photon scattering loss. OCT imaging tools that allow deeper signal penetration with high resolution are still desired in certain medical imaging applications, such as in vivo breast tumor margin assessment for ductal carcinoma in situ (DCIS).

Superluminescent diodes (SLDs) are the most commonly used sources for commercial OCT systems at long wavelength regime (above 1 µm) due to their compactness and cost-effectiveness. However, the SLD's semiconductor gain medium shows an intrinsic trade-off between optical power and bandwidth and they are susceptible to significant bandwidth narrowing due to optical back reflections from fiber facets, lenses or other optical elements. Gain narrowing effects fundamentally limit the FWHM bandwidth and its ability to achieve UHR-OCT in tissue. The 3 dB bandwidth of the superluminescent diode spectrum is normally less than 100 nm and represents a fundamental limitation for the achievable resolution because of the laser gain medium. In addition, careful handling is required due to their sensitivity to electrostatic discharges.

SLDs with a central wavelength of 1300 nm have typical spectral bandwidths of up to 100 nm, corresponding to an axial resolution of 7.7 µm (in air). SLDs with a central wavelength of 800 nm in principle can provide higher resolution, but they have limited signal penetration depth due to Rayleigh scattering and absorption in the biological tissue. Conventional SLDs suffer from the trade-off between the bandwidth and output power, mainly due to the limited gain bandwidth of the optical amplifier medium. While multiplexed SLDs mediate the tradeoff, the irregular shaped spectrum may arouse side lobes in the coherence function and thus reduce the image contrast. A supercontinuum source could also be used to achieve high resolution OCT, but its generation relies on pulsed lasers with kW-range peak power$^2$, which limits its feasibility in a clinical setting. Moreover, as a result of the complex interplay of various nonlinear processes including dispersive wave generation, stimulated Raman scattering, self-phase modulation, four-wave mixing (FWM), supercontinuum sources suffer from high intensity noise that may deteriorate OCT imaging performance.

Current broadband light sources for long-wavelength UHR-OCT are not safe enough to be adopted in clinical settings due to the high optical powers involved in their generation. Specifically, commercial supercontinuum sources used for UHR-OCT require pulsed lasers with kW-range peak power which limits their feasibility in a clinical setting due to laser power safety concerns. Moreover, supercontinuum sources suffer from instabilities in the output intensity and irregularities in the spectral shape as a result of the complex interplay of various nonlinear processes including dispersive wave generation, stimulated Raman scattering, self-phase modulation, four-wave mixing and others.

Improvements are needed.

SUMMARY

Optical coherence tomography (OCT) is a powerful interferometric imaging technique widely used in medical fields such as ophthalmology, cardiology and dermatology. Broadband sources allow for a high resolution imaging down to one micron, and near-infrared (NIR) wavelengths enable imaging depths up to two millimeters in biological tissue. Superluminescent diodes (SLDs) centered at NIR wavelengths are widely used as light sources in OCT. However, they suffer from the tradeoff between bandwidth and output power which limits the achievable resolution and signal penetration depth. Platforms based on chip-scale lithographically-defined microresonators, in accordance with the present disclosure, can break the tradeoff in the conventional SLDs with the potential for sub-micrometer axial resolution and deeper penetration. The proposed platforms are compatible with standard commercial spectral domain (SD) OCT systems and could enable imaging of human tissue with an image quality comparable to the one achieved with SLD. In certain aspects, by multiplexing comb sources and tuning waveguide dimensions, such a system has the capability of achieving resolution down to the sub-micrometer scale. This platform allows for inexpensive and miniaturized sources for OCT and paves the way for UHR-OCT in clinical settings.

Microresonator frequency combs are low-noise broadband sources that cover a wide wavelength range from the visible to the mid-infrared, which in principle can push the limit of OCT axial resolution down to the sub-1 μm regime. Frequency combs have been demonstrated in numerous chip-scale platforms including silica, silicon, silicon nitride, aluminum nitride, crystalline fluorides, diamond and AlGaAs in the past decade. The increasingly high quality factor and dispersion engineering allow for more efficient frequency combs generation and wider optical bandwidth. The conversion efficiency of frequency combs can reach several tens of percent which has the potential to reduce the pump power requirements to a clinic safe regime. The parametric gain in the waveguide structures enables ultra-broad optical bandwidth (up to an octave) and is not limited by the gain bandwidth of a laser medium, which makes chip-based frequency combs fundamentally outperform superluminescent diodes. Another key benefit of microresonators is the precise control of the waveguide's dispersion by cross-section engineering. It allows frequency combs generation over several hundred nanometers, which is highly advantageous for frequency domain OCT applications. Furthermore, the frequency comb lines can be generated in a state where they are not locked in phase by optimizing the cavity resonance detuning relative to the pump frequency. This ensures a low temporal coherence of the comb with high brightness critical for the performance of the OCT.

As the threshold of the frequency combs is inverse to the losses for the chip-based frequency combs, it endows $Si_3N_4$ with the ability to achieve ultra-low loss: One can generate frequency combs with a low power DFB laser which not only significantly reduces the cost and size of the setups, but also reduces the laser power to a safe range for clinical applications. In addition, the chip-based devices can be securely packaged, which will increase the robustness and make them suitable for diversified environments. The chip-scale compact source opens a door for miniaturization of OCT systems.

A compact, robust, low cost, chip-scale platform pumped with inexpensive simple single-frequency continuous-wave diode laser is used to generate frequency combs that can replace the current light source used for OCT. The chip-scale platform for frequency combs that can be ultra-broad (>700 nm) and that enable axial resolution less than 2 μm in air. This platform can be used to generate frequency combs to cover all wavelength ranges needed for OCT, which can lead to a fully integrated on-chip OCT system.

In exemplary embodiments, a microresonator frequency comb is provided comprising a high-Q silicon nitride resonator and a single or multiple distributed feedback (DFB) laser that pumps the resonator to provide a frequency comb source having a bandwidth of 110 nm at 30 dB and a line spacing of 38 GHz. Other materials besides silicon nitride may be used. For example, other materials such as silica, silicon, aluminum nitride, crystalline fluorides, diamond, and AlGaAs, and the like may be used to create the microresonator frequency comb platform. Integrated micro-heaters may also be provided on top of the resonator and configured to provide temperature tuning to control cavity resonance of the resonator. The distributed feedback laser may further comprise a fixed wavelength pump laser. In other exemplary embodiments, a second microresonator frequency comb may be combined with the high-Q silicon nitride resonator on a single chip pumped by the single or multiple distributed feedback laser.

In other exemplary embodiments, a method of providing optical coherence tomography (OCT) imaging is provided comprising using an on-chip frequency comb source interfaced with an OCT system by a circulator as an imaging source and reconstructing OCT images from resulting spectral data from target tissue illuminated by the imaging source. In exemplary methods, reconstructing OCT images includes the steps of background subtraction, linear-k interpolation, apodization, and dispersion compensation of the resulting spectral data from the target tissue.

In still other exemplary embodiments, a method of fabricating a microresonator frequency comb is provided. Such method includes the steps of:

starting from a virgin silicon wafer, growing a 4-um-thick oxide layer for a bottom cladding;

depositing $Si_3N_4$ on the bottom cladding using low-pressure chemical vapor deposition (LPCVD) in steps;

depositing a $SiO_2$ hard mask using plasma enhanced chemical vapor deposition (PECVD) on the $Si_3N_4$;

patterning a resultant device with electron beam lithography;

stripping a resulting resist and oxide mask;

annealing the resultant device at 1200° C. in an argon atmosphere for 3 hours; and cladding the resultant device with 500 nm of high temperature silicon dioxide deposited at 800° C. followed by 2.5 μm of $SiO_2$ using PECVD.

Such a method may further comprise fabricating integrated microheaters above the cladding by sputtering platinum and using a lift-off approach to thermally control the devices. Also, a chemical mechanical planarization and multipass lithography technique may be used to reduce sidewall scattering losses of the resultant device.

BRIEF DESCRIPTION OF THE DRAWINGS

The above and other objects and advantages of the devices and methods described herein will be apparent to those skilled in the art based on the following detailed description in conjunction with the appended figures, of which:

FIG. 1A illustrates a schematic of a microresonator.

FIG. 1B illustrates a microscopy image of the silicon nitride on-chip microresonator, where a platinum heater is fabricated over a large portion of the cavity and allows electric contact via the pads.

FIG. 2A illustrates measured frequency comb spectrum generated using the silicon nitride microresonators, with the solid line showing a simulated frequency comb.

FIG. 2B illustrates measured frequency combs spectrum with broader bandwidth achieved by engineering the waveguide dispersion of the resonator.

FIG. 2C illustrates measured spectrum from a commercial superluminescent diode.

FIGS. 3A-3E illustrates OCT B-scans of human breast tissue taken with (3C) the frequency comb source, (3D) a single SLD source, and (3E) H&E stain. Different features and tissue types, such as stromal tissue, adipose tissue and milk duct, are delineated in both B-scans.

FIG. 4A illustrates a stitched frequency-comb-based OCT B-scan of human coronary artery with a fibrocalcific plaque.

FIG. 4B illustrates H&E histology corresponding to FIG. 4A. Certain features are observed, including fibrous cap thickness, calcium, and media are depicted in OCT images, indicating a great potential for clinic applications.

DETAILED DESCRIPTION OF ILLUSTRATIVE EMBODIMENTS

Figures 5A, 5B:
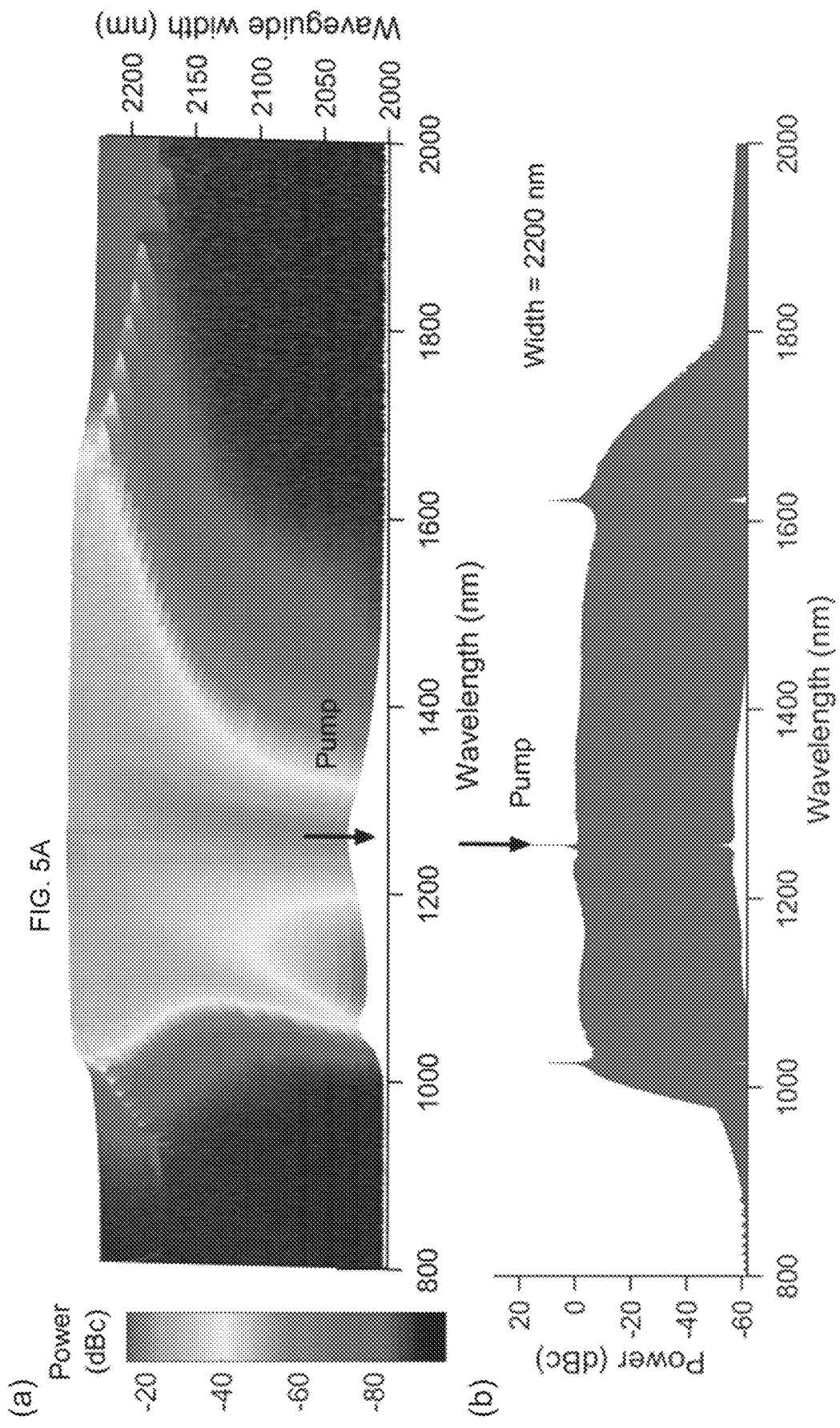
FIG. 5A illustrates a simulated comb spectrum generated from silicon nitride microresonators based on waveguide with a fixed height (710 nm) and varying widths between 2000 nm and 2200 nm. These simulations assume a pump laser wavelength of 1258 nm and power of 100 mW.
FIG. 5B illustrates a simulated ultra-broad flat spectrum generated from a microresonator based on a 2200 nm waveguide width.

An exemplary embodiment of a method and device for providing a microresonator frequency comb platform is described below with respect to FIGS. 1-9. Those skilled in the art will appreciate that the steps and devices described are for exemplary purposes only and are not limited to the specific processes or devices described.

Overview

Achieving microresonator combs with a small line spacing may be desirable for OCT application. In OCT, a spectrometer with a finite spectral resolution is generally used to sample the interferograms, which are Fourier transformed to reconstruct images. If the comb lines are too sparse, it will deteriorate the Fourier-transformed image quality and will reduce the imaging range due to spectrometer resampling requirement. Generating frequency combs with a small line spacing is thus desired for OCT. However, it is challenging to achieve small line spacing due to the large size of the resonator required and the consequently increased parametric oscillation threshold. Also, the presence of mode crossings makes it difficult to achieve a small line spacing yet maintaining a smooth spectrum.

The present disclosure may address one or more shortcomings of the prior art. As described, a microresonator platform may be configured to generate frequency combs with a broad bandwidth of 110 nm and a small line spacing of 38 GHz around the long wavelength OCT imaging window of 1300 nm, based on high-Q silicon nitride resonators. Other configurations may be used.

In certain aspects, favorable results have been achieved using silicon nitride as a material platform to generate broadband micro-resonator frequency combs. Silicon nitride combines the beneficial properties of a wide transparency range covering the entire OCT imaging window, the high nonlinear refractive index ($n_2=2.4\times10^{-19}$ $m^2$/W) and its CMOS compatibility. A majority of the research in silicon nitride broadband frequency combs has been based on devices with a line spacing of 200 GHz or 1 THz, which is too large for many applications including OCT. Other materials besides silicon nitride may be used. For example, other materials such as silica, silicon, aluminum nitride, crystalline fluorides, diamond, and AlGaAs, and the like may be used to create the microresonator frequency comb platform. Additionally, most microresonator combs have been generated with a pump wavelength around 1550 nm, where water absorption is very high, making such combs unsuitable for OCT of biological samples. It will be appreciated by those skilled in the art that the microresonator based frequency combs platform described herein may also be used to generate frequency combs at 800 nm and 1700 nm, in addition to 1550 nm, to cover the full range of OCT operating wavelengths that have the potential to be used widely to replace the current light sources for OCT and to provide better resolution.

In certain aspects, ultra-high-Q resonators may be achieved by minimizing surface roughness of $Si_3N_4$, which not only mitigates undesirable mode crossings but also enables small-line-spacing combs. As an illustrative example, Q may depend on the line spacing. For large line spacing (200G), the present disclosure may achieve Q up to 37 million (loss less than 1 dB/m). For small line spacing (38G) (e.g., using SiN with small line spacing) example results have been about 8 million (loss about 3dB/m). As used herein ultra-high-Q may comprise greater than 800, 000, 900,000, 1 million, 2 million, 3 million, 4 million, 5 million, 6 million, 7 million, 8 million (or intervening end points) using small line spacing of 38G and with large line pacing (200G), losses may be achieved of less than 3 dB/m, less than 2 dB/m, less than 1 dB/m or intervening end points. Other Q factors may be achieved.

In addition, traditional frequency combs are generated based on tabletop ultrafast mode-locked lasers. Microresonators, on the other hand, offer the unique possibility of chip-scale comb sources pumped by stable continuous-wave lasers. Usually these pump lasers are low-noise tunable external cavity diode lasers (ECDLs) which are very expensive, bulky and cumbersome. Due to the low coherence requirement in OCT, the inventors avoid working in the phase locked states which makes it possible to use a simple inexpensive DFB laser to pump the rings. The waveguide cross section is designed to be 1500 nm×730 nm to achieve anomalous dispersion at the pump wavelength. Also, using integrated micro-heaters on top of the devices enables control of the cavity resonance by temperature tuning, which enables using a fixed-wavelength pump laser to generate frequency combs. The platform not only significantly reduces the cost and size of the setups, but also reduces the laser power to a safe range for clinical applications.

A real-time spectral domain (SD) OCT imaging using on-chip frequency combs is demonstrated with a measured axial resolution of 18 µm at 1312 nm, which is better than that achievable with a commercial single superluminescent diode source. The interferogram generated based on the frequency comb source is recorded by a spectrometer. In an exemplary setup of a microresonator frequency comb platform, with the frequency comb source, the axial resolution, measured by the full-width half maximum (FWHM) of the axial point spread function (PSF), is around 18 µm, which matches well with the theoretical estimation of 16.3 µm. This resolution is better than the single external commercialized SLD with a measured axial resolution of 24 µm. Moreover, the frequency combs described herein have the potential to have resolution down to the sub micrometer scale where the pump power needed can be in a clinically safe regime. No other known platform can provide both of these features.

The sensitivity of the OCT system may be defined by the minimal sample reflectivity at which the signal to noise ratio reaches unity. In certain aspects, it is measured to be 100 dB at an A-line rate of 28 kHz for the OCT source. The OCT images are reconstructed from the raw spectral data generated by the system following standard OCT signal processing steps, including background subtraction, linear-k interpolation, apodization, and dispersion compensation.

In other aspects, a platform based on chip-scale lithographically-defined microresonators breaks the tradeoff between bandwidth and output power of conventional SLD sources and could enable OCT with deep tissue penetration and sub-micrometer axial resolution. These microresonators may be fabricated using traditional microelectronic processes. When optically pumped with a single continuous-wave laser source they can generate broadband frequency combs, comprising discrete lines with a frequency spacing determined by the geometry of the resonator. Such frequency combs have been demonstrated in numerous chip-scale platforms including silica, silicon, silicon nitride, aluminum nitride, crystalline fluorides, diamond and AlGaAs. The parametric gain in these photonic structures enables ultra-broad optical bandwidths (up to an octave) in contrast to traditional gain materials and is not limited by the gain bandwidth tradeoff The platforms of the present disclosure may be based on ultra-low loss silicon nitride resonator generated frequency combs with a small line spacing (38 GHz) which is compatible with current OCT spectrometers. FIG. 1a shows the 3D schematics of the resonator and FIG. 1b shows the fabricated on-chip resonator. Silicon nitride has been used extensively to generate broadband microresonator frequency combs. It combines the beneficial properties of a wide transparency range covering the entire OCT imaging window, a high nonlinear refractive index ($n_2=2.4\times10^{-19}$ $m_2/W$),[20] and semiconductor mass manufacturing compatibility. The resonators may be configured with a large cavity length L=1.9 mm so that the frequency comb has a line spacing (0.21 nm) comparable to the spectral sampling interval of the OCT spectrometer (approximately 0.17 nm):

$$\delta\lambda = \frac{\lambda_0^2}{n_g L}, \quad (1)$$

where $\lambda_0$ is the center wavelength, $\delta\lambda$ is the spectral sampling interval, and $n_g$ is the group index. In order to achieve low pump threshold $P_{th}$ given by equation (2) [5,21], $$P_{th} \approx 1.54\left(\frac{\pi}{2}\right)\frac{Q_c}{2Q_L} \cdot \frac{n^2 LA}{n_2 \lambda Q_L^2} \quad (2)$$

where $\lambda$ is the pump wavelength, n and $n_2$ are the linear and nonlinear refractive indices, and A is the cross sectional modal volume. Resonators may be used with ultra-high coupling and loaded quality factors, $Q_c$ and $Q_L$, respectively, and demonstrate frequency combs with a 38-GHz frequency spacing generated using optical pump powers as low as 117 mW. In order to generate the comb with a flat top and adjustable output power, ideal for OCT imaging, the comb generation process may be configured to not induce soliton states with characteristic hyperbolic secant spectrum which limits the achievable FWHM, by tuning of the cavity resonance relative to the pump frequency using a microheater co-fabricated with the resonator. FIG. 2a shows the generated frequency comb spectra with a FWHM of 47 nm, using a ring resonator based on waveguides with 730×1500 nm cross section. This FWHM corresponds to a predicted axial resolution of 16.3 µm (in air) in good agreement with our measured FWHM of the axial point spread function (PSF) of 18 µm (in air). The inset shows the small line spacing of the frequency combs. To show our ability to tailor the spectral shape of these combs by tailoring the dispersion in these resonators, FIG. 2b shows another generated frequency comb spectra with a FWHM of 92 nm, using a ring resonator based on waveguides with slightly different geometries. This FWHM corresponds to a predicted axial resolution of 7.9 µm (in air) which is comparable with the achievable resolution using a single state of art SLD. FIG. 2c shows the spectrum of a single commercial SLD with a FWHM of 28 nm and a measured PSF FWHM of 24 µm (in air) In principle, one can multiplex the comb sources in the same way that multiplexing of SLDs is done. However, other multiplexing methods may be used.

Using the microresonator platform, OCT images of human tissue may be acquired with chip-based frequency combs and show that the platform is compatible with a standard commercial SD-OCT system. These images were achieved using a standard SD-OCT system (Thorlab Telesto I), where the SLD was simply replaced by the chip-based frequency comb. Since the system is not optimized for our combs, the imaging capability is a lower bound limit. FIGS. 3-4 show ex vivo OCT images of human breast and coronary artery samples imaged with our microresonator frequency comb source using a commercial SD-OCT system. The human breast tissue was obtained from Columbia University Tissue Bank[26], and the human heart was obtained via the national disease research interchange[27]. FIG. 3 compares images recorded using our microresonator frequency comb and a commercial SLD which has similar bandwidth of the generated combs. The Hematoxylin and Eosin (H&E) stained histology is provided as the reference for both the breast and coronary artery tissue structures. Different tissue types, including stromal tissue, adipose tissue and milk duct, are delineated in both B-scans by comparing with the corresponding histology analysis. FIG. 4a shows a stitched frequency-comb-based OCT image of a human left anterior descending artery (LAD) in comparison with the H&E histology in FIG. 4b. OCT B-scans were stitched using the method previously used in cervical imaging. In the red inset, a gradually decreasing trend of backscattering can be visualized within the transition region from a fibrous region to the media. The blue inset in FIG. 4 reveals a typical pattern of a fibrocalcific plaque[3], where a layer of signal-rich fibrous cap is on the top of calcium, a signal-poor region with a sharply delineated border. Importantly, overlying the fibrocalcific plaque region, a transition can be seen from dense fibrous cap for stable plaque structure to thinner fibrous cap for unstable plaque structure, the latter of which is highly correlated with acute coronary syndrome and acute myocardial infarction. FIG. 4 indicates the potential to visualize critical features in human coronary arteries by integrating the chip-based frequency combs into an OCT system.

Figure 6:
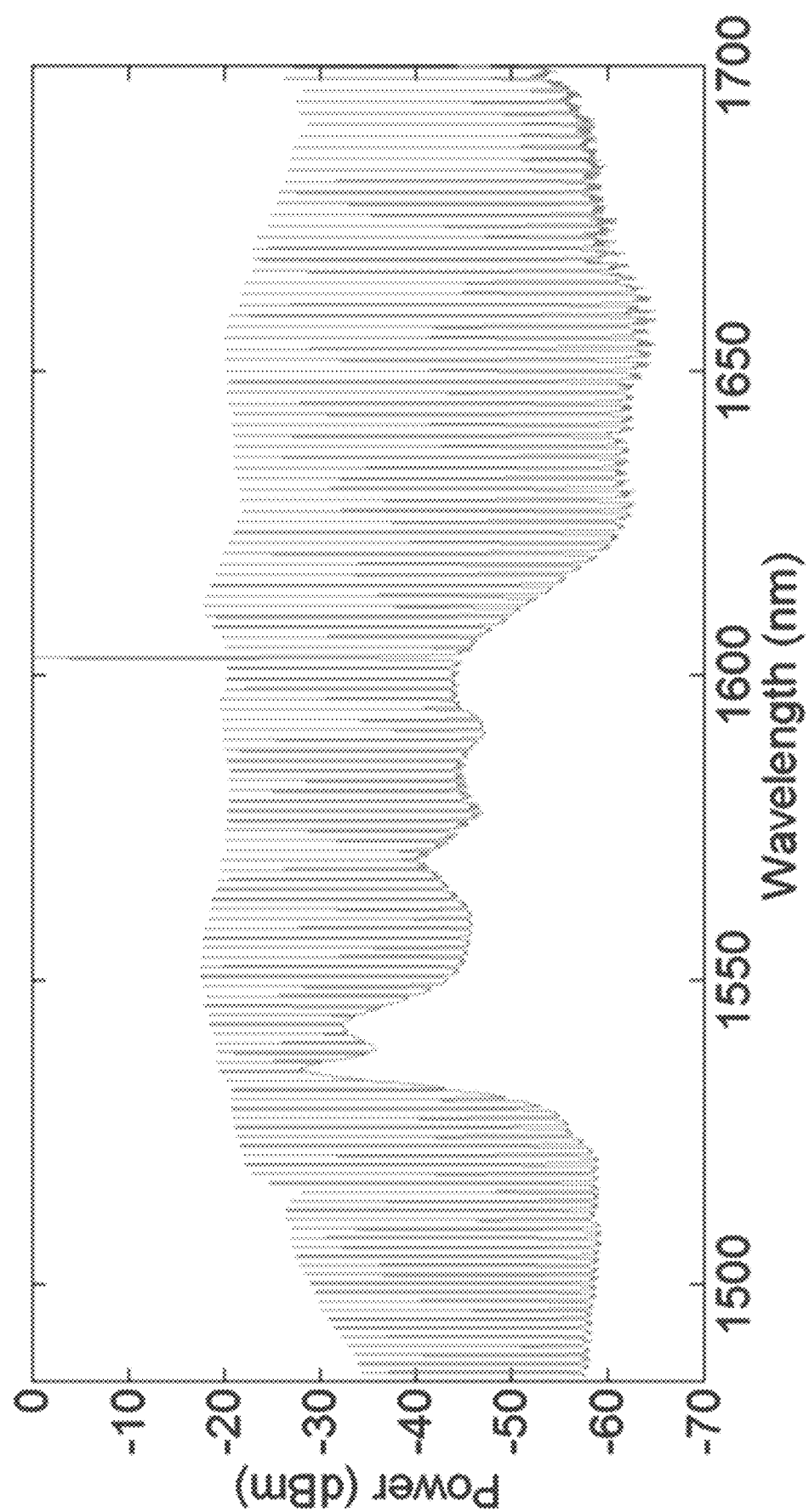
FIG. 6 illustrates measured frequency comb spectrum generated using designed silicon nitride microresonators centered around 1600 nm with FWHM of 154 nm (corresponding to resolution of 7.3 um in air).

OCT based on microresonator frequency combs has the capability of achieving resolution below 1 μm simply by engineering the waveguide dimensions of the resonator. In order to tune the waveguide dispersion and achieve wide spectral combs, the geometry of the waveguide may be configured to compensate for higher-order waveguide dispersion effects. A flat uniform spectrum with even broader spectrum of several hundred nanometers could be generated from a single frequency comb (simulation is shown in FIG. 5). In FIG. 6, combs are shown generated around 1600 nm with FWHM of 154 nm achieved using such compensation. The efficiency of these combs can be up to 30%, enabling simultaneous high output power and broad bandwidth, in contrast to the traditional SLD sources which suffer from power-bandwidth tradeoff.

In conclusion, a microresonator frequency comb platform is shown that has the potential for paving the way for UHR-OCT in clinical settings. The frequency comb is generated using high-Q silicon nitride resonators. The capability of frequency comb OCT imaging is illustrated by comparing with the histology analysis. The platform has the potential to be cost-effective. In order to generate these frequency combs, a pump source may be used based on a low-cost distributed feedback (DFB) laser in contrast to the high power and high stability wavelength-tunable sources usually required for generating phase-locked frequency combs. The integration of such laser with our microresonator platform could enable inexpensive sources for clinically safe OCT and allow for miniaturization of OCT systems.

Device Fabrication

Starting from a silicon wafer, a 4-um-thick oxide layer is grown for the bottom cladding. Silicon nitride ($Si_3N_4$) is deposited using low-pressure chemical vapor deposition (LPCVD) in steps. After $Si_3N_4$ deposition, a silicon dioxide ($SiO_2$) hard mask may be deposited using plasma enhanced chemical vapor deposition (PECVD). Patterning may be accomplished using JEOL 9500 electron beam lithography. Ma-N 2403 electron-beam resist is used to write the pattern and the nitride film is etched in an inductively coupled plasma reactive ion etcher (ICP RIE) using a combination of $CHF_3$, $N_2$, and $O_2$ gases. After stripping the resist and oxide mask, the devices may be annealed at 1200° C. in an argon atmosphere for 3 hours to remove residual N—H bonds in the $Si_3N_4$ film. The devices may be clad with 500 nm of high temperature silicon dioxide (HTO), deposited at 800° C., and followed by 2.5 μm of $SiO_2$ using PECVD. CMP and multipass lithography technique can be applied to further reduce sidewall scattering losses. Above the waveguide cladding, integrated microheaters may be fabricated by sputtering platinum and using a lift-off approach. Microheaters may be integrated on our device to control the cavity resonance by temperature tuning, which enables the use of a simple compact single-frequency pump laser diode to generate frequency combs.

Measurements

Figure 7:
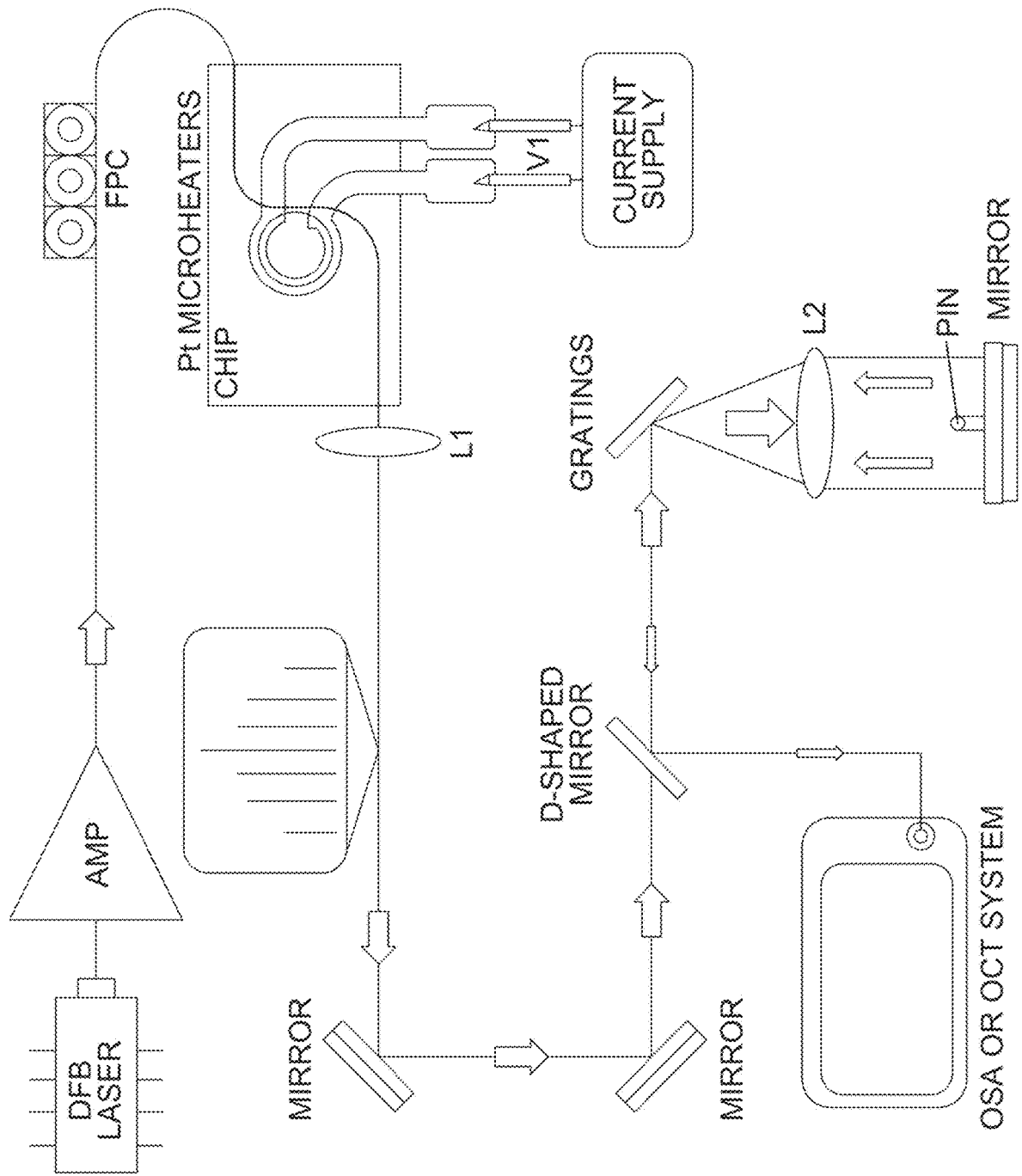
FIG. 7 illustrates a system setup for comb generation and pump filtering. A DFB laser is amplified and coupled to the $Si_3N_4$ micro-chip. On-chip heater allows thermal control of the cavity to ensure comb generation with low coherence. A grating is used to filter out the pump laser before the comb is sent to the OCT system.
Figure 8:
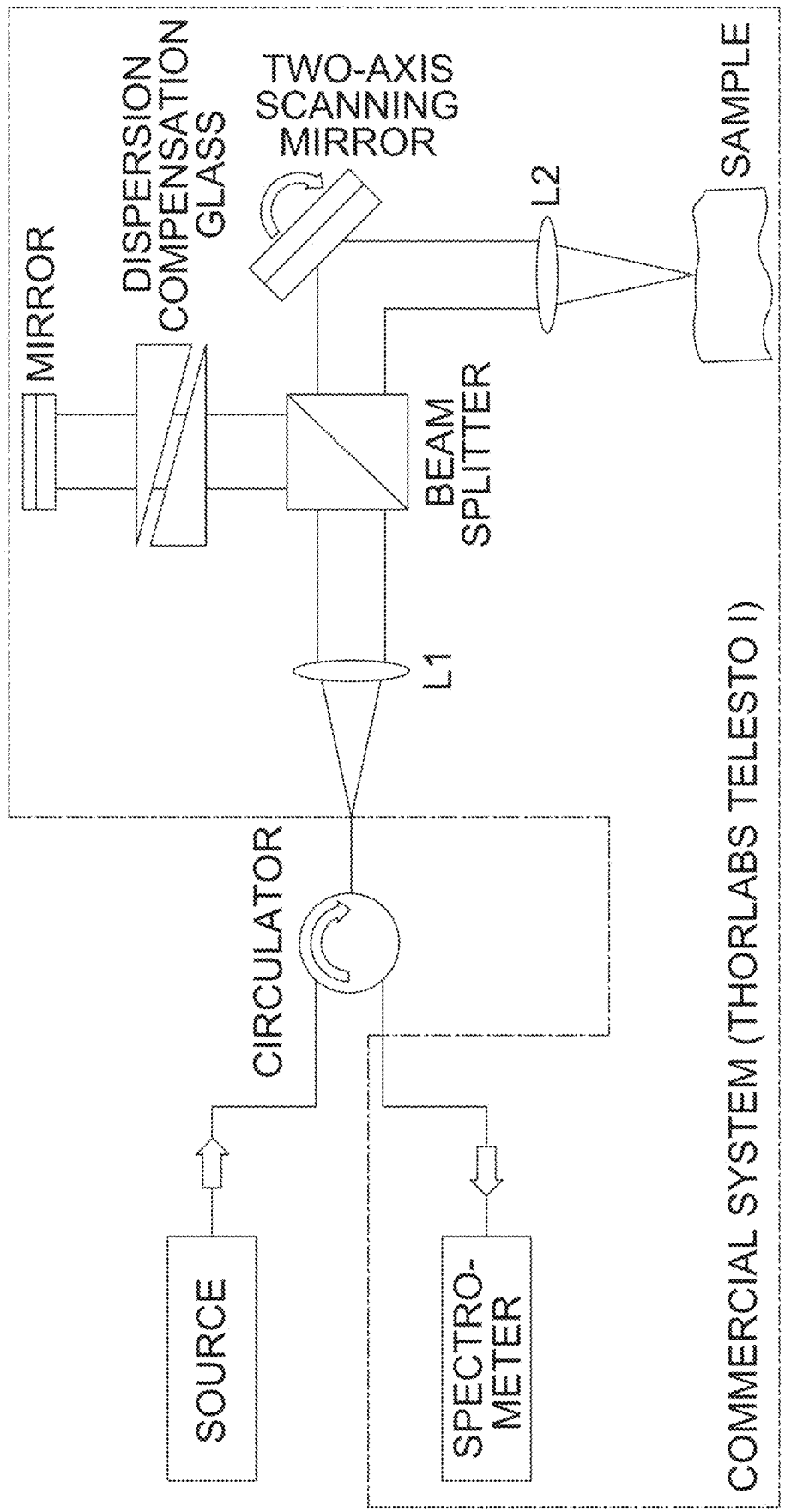
FIG. 8 illustrates a schematic of the comb-based OCT setup. The fiber coupled light source is sent into a circulator, from which the beam is first collimated in free space and then split for the two OCT interferometer arms. The reference arm includes glass prisms to control dispersion. In the sample arm the beam reflects off a fast scanning mirror and is sent to the sample for imaging. The back-scattered light is collected and sent to the OCT spectrometer for image generation.

As the presence of the pump within the comb spectrum limits the dynamic range of the detection, a filtering setup may be used based on a free-space grating and pin to fully attenuate the pump power. The setup is shown in FIG. 7. This filtering setup can be replaced by a customized fiber-based filter to miniaturize the size of the setup in the future. The output power of our optical frequency comb source may be adjusted to be similar to the output power of the SLD being used. The comb source may be coupled directly into a commercial system (Thorlabs Telesto I) to acquire images. The schematic of the OCT system is shown in FIG. 8. An optical circulator with an isolation of −40 dB is added to protect the commercial console. The incident light from the comb source is routed to the Michelson interferometer, and the backscattered signals from both interferometer arms are directed back to the spectrometer.

Using the frequency combs combined with the commercialized SD-OCT system, OCT images may be acquired. The images are reconstructed in real-time from the raw spectral data generated by the system, following standard OCT signal processing steps, including background subtraction, linear-k interpolation, apodization, and dispersion compensation. The acquisition rate is 28 kHz currently limited by the CCD line rate. The total acquisition time of an image for the SLD and the chip comb images is the same (35 msec). The sensitivity of the OCT system is defined by the minimal sample reflectivity at which the signal to noise ratio reaches unity. It is measured to be 100 dB at an A-line rate of 28 kHz for the frequency comb source. The sensitivity can be further increased by suppressing the noise due to the laser-chip coupling via packaging.

Ultra-Board Frequency Comb Spectrum Simulation

FIG. 5 shows a simulated frequency comb spectrum generated from silicon nitride microresonators. It shows the potential for generating a flat uniform spectrum over several hundred nanometers by engineering the geometry of the waveguide to compensate for higher-order waveguide dispersion effects.

Frequency Comb Spectrum Generated Centered around 1600 nm

FIG. 6 shows a measured frequency comb spectrum generated centered around 1600 nm with FWHM of 154 nm. This frequency comb is generated using the same silicon nitride microresonators platform.

System Setup

FIG. 7 shows the system setup for comb generation and pump filtering. A DFB laser is amplified and coupled to the $Si_3N_4$ micro-chip. An amplifier may be used to compensate coupling loss from the setup. A grating is used to filter out the pump laser before the comb is sent to the OCT system. This filtering setup can be replaced by a customized fiber-based filter to miniaturize the size of the setup in the future.

FIG. 8 shows the schematic of the comb-based OCT setup. Note that the comb source is directly coupled into the commercial system (Thorlabs Telesto I) to acquire images. The optical circulator is added to protect the commercial console. It shows that our platform is compatible with a standard commercial SD-OCT system.

A Line Analysis and Noise Discussion

Figure 9A:
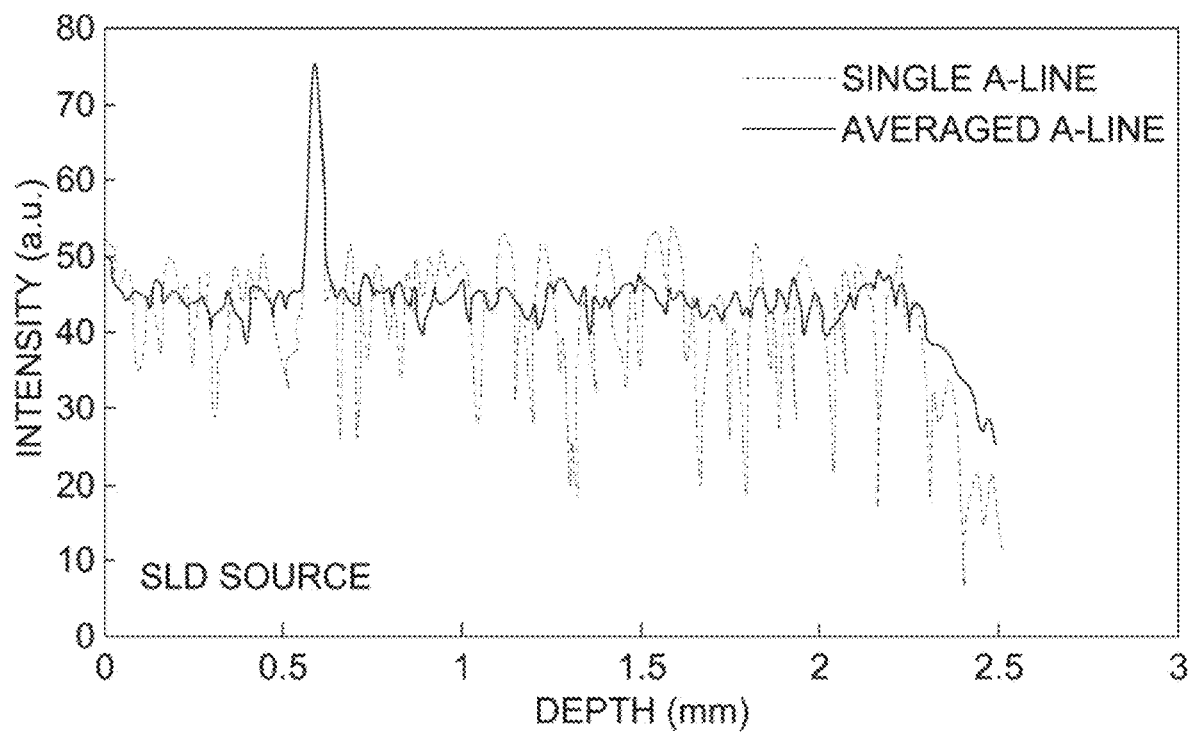
FIGS. 9A-9B illustrate A-line profiles of a mirror surface measured with SLD and comb sources, respectively. The SLD and comb source have the same acquisition rate. Single A lines are shown in gray and A lines obtained by 10× averaging (corresponding to a total of 357 μs acquisition time in current setting) are shown in blue. One can see that the noise level of the comb source is comparable to the level of SLD's and can be further reduced by suppressing the noise due to the laser-chip coupling via packaging.
Figure 9B:
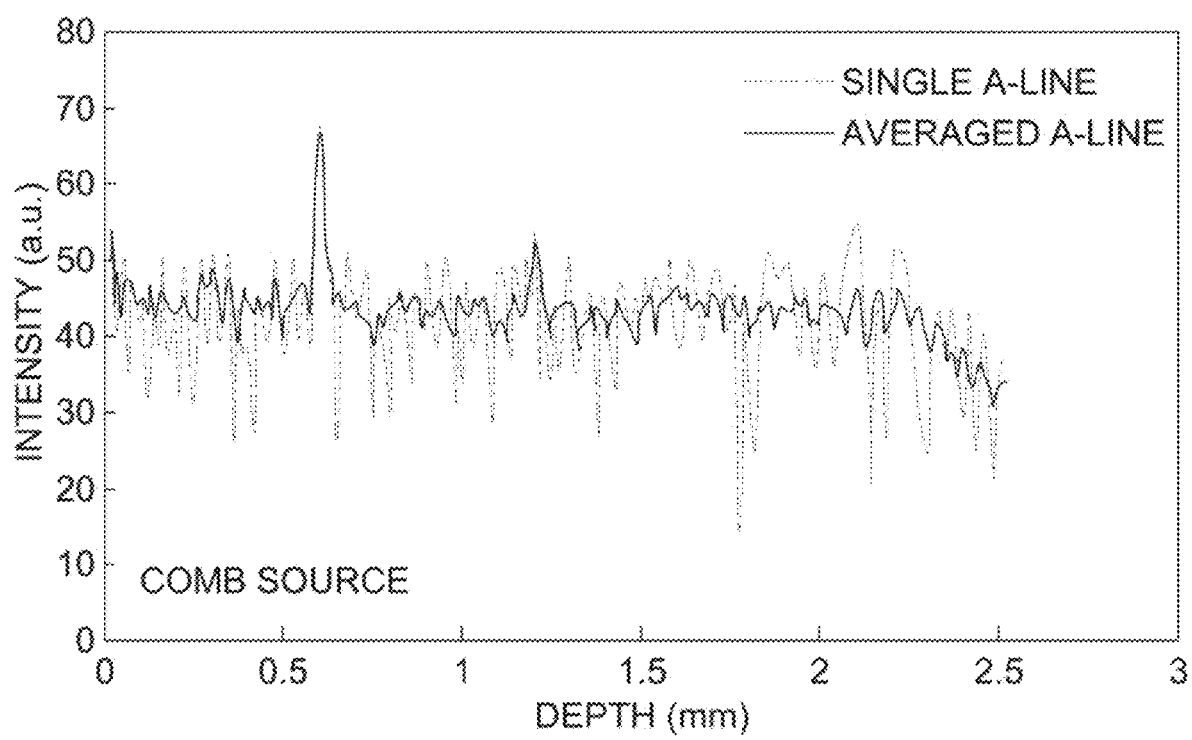

FIG. 9 shows the A-line signals extracted from OCT B-scan images of a mirror surface, taken with an SLD and the comb source, respectively. From the figure, one can see that the discrete nature of combs does not deteriorate the OCT images quality. The SLD and comb source have the same acquisition rate of 28 kHz (limited by the CCD line rate). One can see that the noise level of the comb source is comparable to the level of SLD's indicating that the expected extra noise in the comb setup from fiber coupling setup, known to induce extra noise due to fiber fluctuations, has a minimal effect on the OCT imaging capabilities. If needed, any extra noise from the coupling can be significantly suppressed by packaging the source with the chip.

The techniques disclosed herein demonstrate a microresonator frequency comb platform for OCT applications. Those skilled in the art will appreciate that the techniques described herein may be used for other applications as well. For example, the platform may be used for replacing commercial supercontinuum sources. Such sources use microstructural fibers (such as photonic crystal fibers) for supercontinuum generation, which is a result of a complex interplay of various nonlinear processes, including simulated Raman scattering, self-phase modulation, four-wave mixing and others.

The invention claimed is:

1. A microresonator frequency comb comprising:
   one or more lasers; and
   a high-Q resonator comprising silicon nitride, wherein the high-Q resonator is pumped by the one or more lasers to provide a frequency comb source configured as an imaging source for an optical coherence tomography (OCT) system, and wherein the high-Q resonator is tuned to control a resonance of the resonator relative to a frequency of a pump signal of the one or more lasers.

2. The microresonator frequency comb of claim 1, further comprising integrated micro-heaters configured to provide temperature tuning to control cavity resonance of said resonator.

3. The microresonator frequency comb of claim 2, wherein a micro-heater comprises platinum.

4. The microresonator frequency comb of claim 1, wherein the one or more lasers comprise a fixed wavelength pump laser.

5. The microresonator frequency comb of claim 1, wherein the one or more lasers comprise one of a distributed feedback (DFB) laser, an external cavity laser, or a Fabry-Perot laser.

6. The microresonator frequency comb of claim 5, wherein the laser comprises a distributed feedback (DFB) laser and further comprising a second microresonator frequency comb combined with said high-Q resonator on a single chip and pumped by said distributed feedback (DFB) laser.

7. The microresonator frequency comb of claim 1, further comprising a waveguide configured to couple light from the one or more lasers to the resonator.

8. The microresonator frequency comb of claim 7, wherein the waveguide comprises silicon nitride.

9. The microresonator frequency comb of claim 7, wherein the waveguide comprises silica, silicon, aluminum nitride, crystalline fluorides, diamond, or AlGaAs.

10. The microresonator frequency comb of claim 1, wherein the frequency comb source has a bandwidth of 110 nm at 30 dB and a line spacing of 38 GHz.

11. The microresonator frequency comb of claim 1, wherein the resonator exhibits a Q of up to 37 million.

12. The microresonator frequency comb of claim 11, wherein the resonator exhibits a Q of up to 8 million.

13. The microresonator frequency comb of claim 1, wherein the resonator exhibits a loss of from 3 dB/m to 1 dB/m.

14. The microresonator frequency comb of claim 1, wherein the resonator exhibits a loss of less than 3 dB/m.

15. The microresonator frequency comb of claim 1, wherein the resonator has a line spacing of from about 38 GHz to about 200 GHz.

16. The microresonator frequency comb of claim 1, wherein the high-Q resonator has a Q value in a range of from $8+10^5$ to $3.7\times10^7$.

17. An optical coherence tomography system comprising:
   a microresonator frequency comb comprising:
      one or more lasers; and
      a high-Q resonator comprising silicon nitride, wherein said high-Q resonator is pumped by the one or more lasers to provide a frequency comb source configured as an imaging source, and wherein the high-Q resonator is tuned to control a resonance of the resonator relative to a frequency of a pump signal of the one or more lasers; and
   a computing device configured to generate images using signals received based on signals produced by the microresonator frequency comb.

18. The optical coherence tomography system of claim 17, wherein the system has an axial resolution of about 18 µm.

19. The optical coherence tomography system of claim 17, wherein the system has a sensitivity of 100 dB at an A-line rate of 28 kHz for the frequency comb source.

20. The optical coherence tomography system of claim 17, further comprising a grating configured to filter out the pump signal before the frequency comb is communicated to the optical coherence tomography system.

* * * * *